(12) United States Patent
Fujii et al.

(10) Patent No.: US 7,815,958 B2
(45) Date of Patent: Oct. 19, 2010

(54) CAROTENOIDS COLOR EMULSION PREPARATION

(75) Inventors: Kazuyuki Fujii, Toyonaka (JP); Norihiko Inada, Toyonaka (JP)

(73) Assignee: San-Ei Gen F.F.I., Inc., Toyonaka-Shi (JP)

( * ) Notice: Subject to any disclaimer, the term of this patent is extended or adjusted under 35 U.S.C. 154(b) by 167 days.

(21) Appl. No.: 11/984,202

(22) Filed: Nov. 14, 2007

(65) Prior Publication Data

US 2008/0124435 A1 May 29, 2008

Related U.S. Application Data

(62) Division of application No. 10/479,976, filed as application No. PCT/JP02/05975 on Jun. 14, 2002, now abandoned.

(30) Foreign Application Priority Data

Jun. 14, 2001 (JP) ............................. 2001-180367

(51) Int. Cl.
*A23L 1/27* (2006.01)
(52) U.S. Cl. ........................ 426/590; 426/250; 426/270; 426/443; 426/520; 426/573; 426/601; 426/602; 426/654
(58) Field of Classification Search ................ 426/250, 426/590, 573, 654, 601, 602, 270, 520, 443
See application file for complete search history.

(56) References Cited

U.S. PATENT DOCUMENTS

| 5,382,714 A | 1/1995 | Khachik |
| 5,648,564 A | 7/1997 | Ausich et al. |
| 5,897,866 A | 4/1999 | Bombardelli et al. |
| 6,235,315 B1 | 5/2001 | Runge et al. |

FOREIGN PATENT DOCUMENTS

| EP | 0732378 | 9/1996 |
| JP | 56-11961 A | 2/1981 |
| JP | 59-033259 | 2/1984 |
| JP | 61-264061 A | 11/1986 |
| JP | 63-039966 | 2/1988 |
| JP | 63-258558 | 10/1988 |
| JP | 08-092205 | 4/1996 |
| JP | 8-168356 A | 7/1996 |
| JP | 08-253695 | 10/1996 |
| JP | 9-157537 | 6/1997 |
| JP | 10-226654 | 8/1998 |
| JP | 11-508603 | 7/1999 |
| JP | 11-322708 | 11/1999 |
| JP | 2000-290525 | 10/2000 |

OTHER PUBLICATIONS

Japanese Office Action dated Feb. 25, 2009.
International Search Report dated Aug. 27, 2002.

*Primary Examiner*—Helen F Pratt
(74) *Attorney, Agent, or Firm*—Kratz, Quintos & Hanson, LLP

(57) ABSTRACT

The present invention provides a carotenoids color preparation which itself has a high emulsion stability, so that there are no problems such as precipitation of an insoluble matter or neck ring formation even when this preparation is used in water-based products. The preparation is obtained by emulsifying a carotenoids color of natural origin, which has an acid value of 10 or less and an acetone-insoluble content of 5 wt % or less when adjusted so that the color value $E^{10\%}_{1cm}$ is 2550.

7 Claims, No Drawings

CAROTENOIDS COLOR EMULSION PREPARATION

CROSS REFERENCE TO RELATED APPLICATIONS

This application is a divisional of U.S. Ser. No. 10/479,976, filed on Dec. 12, 2003, now abandoned, which is a 371 of PCT/JP02/05975, filed on Jun. 14, 2002, which is hereby incorporated by reference.

TECHNICAL FIELD

The present invention relates to an emulsified color preparation. In concrete terms, the present invention relates to a carotenoids color preparation which is prepared by emulsifying a carotenoids color, which is an oily color originating in natural raw materials, so that this color preparation can be widely used in various types of products such as food products, drugs, quasi-drugs, cosmetics, products for daily use, feeding stuffs and the like, and especially in water-based products. More particularly, the present invention relates to an emulsion preparation of a carotenoids color (referred to as a "carotenoids color emulsion preparation" in the present specification) which has a high emulsion stability in itself, and which is superior in terms of the stability of the prepared emulsion, so that there are no problems such as neck ring formation, precipitation or the like when this preparation is used in water-based products.

Furthermore, the present invention also relates to a carotenoids color used in the manufacture of the abovementioned carotenoids color preparation, a method for manufacturing this carotenoids color preparation, and various applications of this carotenoids color preparation.

BACKGROUND ART

A carotenoids color is oily based color. Accordingly, the color has conventionally been prepared as an aqueous dispersion type preparation (an emulsified color preparation) using an emulsification technique so that the color can be widely used in the coloring of water-based products such as beverages and the like. However, the carotenoids color originating in a natural raw material generally contains large quantities of impurities such as free fatty acids, phospholipids, gum substances and the like originating in such raw material, and is therefore difficult to emulsify, or may show poor storage stability (emulsion stability) even when successfully emulsified. Accordingly, it has conventionally been difficult to obtain a color preparation that contains a carotenoids color in large quantities, i.e., at a high concentration. Furthermore, for the abovementioned reasons, the following problem has also been encountered: namely, in cases where a carotenoids color emulsion preparation is used in a water-based product such as beverages or the like, neck ring formation or precipitation tends to occur as a result of particle deterioration.

Conventionally, the following methods have been known as methods for removing impurities originating in natural raw materials from the carotenoids color: specifically, a method in which an oleo resin obtained by extracting an oil and fat fraction containing the carotenoids color with an organic solvent is hydrolyzed using an alkali, and the carotenoids color is extracted and recovered from the resulting hydrolysis product using an organic solvent (Japanese published examined patent application No. 52-3741), a method in which a mineral acid is added to a preparation obtained by treating an oleo resin containing a carotenoids color with an alkali, and the carotenoids color is recovered by subjecting the carotenoids color-containing substance thus obtained to molecular distillation (Japanese published examined patent application No. 61-52184), a method in which a mixed raw material of a natural carotenoids color and an oil and fat are subjected to a hydrolysis treatment, this hydrolysis product is subjected to an extraction using d-limonene or the like, and the carotenoids color is recovered by removing the d-limonene or the like from the extract under specified conditions (Japanese published un-examined patent application No. 1-290659), and the like.

DISCLOSURE OF THE INVENTION

It is an object of the present invention to solve the abovementioned problems that occur when a carotenoids color of natural origin is used as a raw material for the manufacture of an aqueous dispersion type preparation (an emulsified color preparation).

First, in concrete terms, it is an object of the present invention to provide a carotenoids color emulsion preparation that is superior in terms of emulsion stability, and a carotenoids color that can be used in the manufacture of such a preparation.

Secondly, it is an object of the present invention to provide a method for manufacturing the abovementioned carotenoids color emulsion preparation that is superior in terms of emulsion stability.

Thirdly, it is an object of the present invention to provide an emulsion stabilizing method for a carotenoids color emulsion preparation.

Fourth, it is an object of the present invention to provide products colored using a carotenoids color emulsion preparation, in which the occurrence of neck ring formation, deposition (precipitation) of insoluble matter and the like are significantly suppressed.

As a result of diligent research, the present inventors discovered that the abovementioned problems could be solved by using a carotenoids color of natural origin that has a specified constitution as a raw material for a carotenoids color emulsion preparation. The present invention was developed on the basis of this finding.

I. Specifically, the present invention is the carotenoids color described in the following item 1:

Item 1. A carotenoids color of natural origin, which has an acid value of 10 or less and an acetone-insoluble content of 5 wt % or less when adjusted so that the color value $E^{10\%}_{1cm}$ is 2550.

The following aspects are included in the carotenoids color of the present invention:

(1-1) The carotenoids color according to item 1, wherein the acid value is 5 or less, and the acetone-insoluble content is 2 wt % or less.

(1-2) The carotenoids color according to item 1, wherein the carotenoids color is acquired by treating a carotenoid extract obtained from a carotenoid-containing animal or plant or carotenoid-producing microorganism by at least one method selected from the following methods:

(i) a method in which an extraction is performed using an oil and fat or an organic solvent, (ii) a method in which hydrolysis is performed using an alkali, and residual matter is removed by rinsing with water, (iii) a method in which an acid or water is added and heated, and gum substances and proteins are removed by centrifugation, (iv) a method in which a lower monoalcohol is added and alcoholysis is performed to produce a carotenoid-containing fatty acid lower alkyl ester, and residual matter is then removed by rinsing with water, (v) a method in which washing is performed with a hydrophilic solvent, the carotenoid thus obtained is dissolved in cold acetone, and residual matter is removed by deposition, (vi) a method in which purification is performed using a molecular distillation apparatus, and (vii) a method in which an extraction is performed by means of a supercritical fluid using carbon dioxide.

The abovementioned carotenoids color is useful as a raw-material color for the carotenoids color emulsion preparations described below.

II. The emulsified color preparations described in the following items 2 through 7 may be cited as examples of carotenoids color emulsion preparations.

Item 2. A carotenoids color emulsion preparation obtained by emulsifying and preparing a carotenoids color of natural origin which has an acid value of 10 or less and an acetone-insoluble content of 5 wt % or less when adjusted so that the color value $E^{10\%}_{1cm}$ is 2550.

Item 3. The carotenoids color emulsion preparation according to item 2, which is prepared by a method comprising the following processes:

(i) a process in which, if necessary an oil and fat is mixed with a carotenoids color, a carotenoids color or the above-obtained mixture is heated and dissolved so that an oil phase component is prepared, (ii) a process in which an emulsifying agent and an aqueous phase component are mixed with the oil phase component obtained in the abovementioned process (i), and (iii) a process in which the mixture obtained in the abovementioned process (ii) is emulsified.

Item 4. The carotenoids color emulsion preparation according to item 3, which is further prepared by a method comprising (iv) a process in which the emulsified product in liquid form obtained in the abovementioned process (iii) is dried, or a process in which this product is granulated.

Item 5. The carotenoids color emulsion preparation according to any of items 2 through 4, which is a color preparation having a liquid-form, powder-form or granular configuration.

Item 6. The carotenoids color emulsion preparation according to any of items 2 through 5, which contains a carotenoids color at the rate of 0.01 to 50 wt % per 100 wt % of the carotenoids color emulsion preparation.

Item 7. The carotenoids color emulsion preparation according to any of items 2 through 6, wherein the carotenoids color used as a raw material is at least one color selected from dunaliella carotene, carrot carotene, palm oil carotene, tomato color, marigold color, paprika color, hematococcus algae color, orange color, Krill color, and phaffia color.

The following aspects are included in the carotenoids color emulsion preparation of the present invention:

(II-1) The carotenoids color emulsion preparation according to any of items 2 through 7, wherein the carotenoids color used as a raw material has an acid value of 5 or less and an acetone-insoluble content of 2 wt % or less when adjusted so that the color value $E^{10\%}_{1cm}$ is 2550.

(II-2) The carotenoids color emulsion preparation according to any of items 2 through 7, which contains a carotenoids color at the rate of 0.05 to 40 wt %, preferably 0.1 to 30 wt %, per 100 wt % of the carotenoids color emulsion preparation.

(II-3) The carotenoids color emulsion preparation according to any of items 2 through 7, which contains a carotenoids color at the rate of 10 to 50 wt %, 15 to 50 wt % or 20 to 50 wt % per 100 wt % of the carotenoids color emulsion preparation.

(II-4) The carotenoids color emulsion preparation according to any of items 2 through 7, wherein the carotenoids color used as a raw material is prepared by treating a carotenoid extract obtained from a carotenoid-containing animal or plant or carotenoid-producing microorganism by at least one method selected from the following methods:

(1) a method in which an extraction is performed using oil and fat or an organic solvent, (2) a method in which hydrolysis is performed using an alkali, and residual matter is removed by rinsing with water, (3) a method in which an acid or water is added and heated, and gum substances and proteins are removed by centrifugation, (4) a method in which a lower monoalcohol is added and alcoholysis is performed to produce a carotenoid-containing fatty acid lower alkyl ester, and residual matter is then removed by rinsing with water, (5) a method in which washing is performed with a hydrophilic solvent, the carotenoid thus obtained is dissolved in cold acetone, and residual matter is removed by deposition, (6) a method in which purification is performed using a molecular distillation apparatus, and (7) a method in which an extraction is performed by means of a supercritical fluid using carbon dioxide.

In the case of the carotenoids color emulsion preparation of the present invention, since the preparation itself is superior in terms of emulsion stability, the carotenoids color can be stably contained in this emulsion preparation even if the quantity of this carotenoids color is large. Specifically, the present invention makes it possible to provide a color preparation that can contain a carotenoids color at a high concentration. Using this high-concentration color preparation, objects can be colored with a small quantity of the preparation; accordingly, the problem of odorizing that may original in the color preparation can be significantly resolved.

Generally, in cases where emulsified color preparations prepared from carotenoids colors of natural origin are used for the coloring of water-based products such as beverages or the like, the problems of neck ring formation and precipitation arise as a result of the deterioration of the emulsified particles. However, if the abovementioned carotenoids color emulsion preparation of the present invention is used, the following advantage is obtained: namely, since such deterioration of the emulsified particles is significantly suppressed, the abovementioned phenomena of neck ring formation, precipitation and the like tend not to occur.

III. Furthermore, the present invention also provides a colored product described in the following items 8 or 9, which is prepared using the abovementioned carotenoids color emulsion preparation.

Item 8. A product selected from food products, drugs, quasi-drugs, cosmetics, products for daily use and feeding stuffs which is colored using the carotenoids color emulsion preparation according to any of items 2 through 7.

Item 9. The product described in item 8, which is a food product.

The abovementioned colored products are products in which the abovementioned carotenoids color emulsion preparation of the present invention is used as a colorant. In cases where a color preparation containing a high concentration of a carotenoids color is used as the abovementioned colorant in the colored products of the present invention, a small amount of this preparation is sufficient; accordingly, adhering of odors originating in the color preparation can be significantly suppressed. Furthermore, in cases where the colored product of the present invention is a water-based product such as a cold confection (especially an iced confection), beverage, lotion, emulsion or the like, the following merit can also be obtained: namely, the occurrence of phenomena such as neck ring formation and precipitation (deposition of insoluble matter) caused by deterioration of the emulsified particles can be significantly suppressed.

IV. Furthermore, the present invention also provides methods for manufacturing the carotenoids color emulsion preparation, as described in the following items 10 through 13:

Item 10. A method for manufacturing a carotenoids color emulsion preparation which uses as a raw material a carotenoids color of natural origin that has an acid value of 10 or less and an acetone-insoluble content of 5 wt % or less when adjusted so that the color value $E^{10\%}_{1cm}$ is 2550, and which comprises an emulsification of the carotenoids color.

Item 11. The method for manufacturing a carotenoids color emulsion preparation according to item 10, wherein the carotenoids color, which has an acid value of 10 or less and an acetone-insoluble content of 5 wt % or less when adjusted so that the color value $E^{10\%}_{1cm}$ is 2550, is acquired by treating a carotenoid extract obtained from a carotenoid-containing animal or plant or carotenoid-producing microorganism by at least one method selected from the following methods:

(1) a method in which an extraction is performed using oil and fat or an organic solvent, (2) a method in which hydrolysis is performed using an alkali, and residual matter is removed by rinsing with water, (3) a method in which an acid or water is added and heated, and gum substances and proteins are removed by centrifugation, (4) a method in which a lower monoalcohol is added and alcoholysis is performed to produce a carotenoid-containing fatty acid lower alkyl ester, and residual matter is then removed by rinsing with water, (5) a method in which washing is performed with a hydrophilic solvent, the carotenoid thus obtained is dissolved in cold acetone, and residual matter is removed by deposition, (6) a method in which purification is performed using a molecular distillation apparatus, and (7) a method in which an extraction is performed by means of a supercritical fluid using carbon dioxide, and by emulsifying the carotenoids color thus obtained.

Item 12. The method for manufacturing a carotenoids color emulsion preparation according to item 10 or item 11, which comprises the following processes:

(i) a process in which, if necessary an oil and fat is mixed with a carotenoids color, a carotenoids color or the above-obtained mixture is heated and dissolved so that an oil phase component is prepared, (ii) a process in which an emulsifying agent and an aqueous phase component are mixed with the oil phase component obtained in the abovementioned process (i), and (iii) a process in which the mixture obtained in the abovementioned process (ii) is emulsified.

Item 13. The method for manufacturing a carotenoids color emulsion preparation according to item 12, which further comprises (iv) a process in which the emulsified product in liquid form obtained in the abovementioned process (iii) is dried, or a process in which the product is granulated.

The following aspects are included in the method of the present invention for manufacturing a carotenoids color emulsion preparation:

(IV-1) The method for manufacturing a carotenoids color emulsion preparation according to any of items 10 through 13, wherein the carotenoids color used as a raw material is a color which has an acid value of 5 or less and an acetone-insoluble content of 2 wt % or less when adjusted so that the color value $E^{10\%}_{1cm}$ is 2550.

V. Furthermore, the present invention also provides the methods for stabilizing the emulsification of a carotenoids color emulsion preparation, as described in the following items 14 through 16:

Item 14. A method for stabilizing the emulsification of a liquid-form carotenoids color emulsion preparation, wherein a carotenoids color of natural origin which has an acid value of 10 or less and an acetone-insoluble content of 5 wt % or less when adjusted so that the color value $E^{10\%}_{1cm}$ is 2550 is used as the raw-material carotenoids color that is emulsified.

Item 15. The method for stabilizing the emulsification of a liquid-form carotenoids color emulsion preparation according to item 14, wherein the carotenoids color as a raw-material carotenoids color that is emulsified, which has an acid value of 10 or less and an acetone-insoluble content of 5 wt % or less when adjusted so that the color value $E^{10\%}_{1cm}$ is 2550, is acquired by treating a carotenoid extract obtained from a carotenoid-containing animal or plant or carotenoid-producing microorganism by at least one method selected from the following methods:

(1) a method in which an extraction is performed using an oil and fat or an organic solvent, (2) a method in which hydrolysis is performed using an alkali, and residual matter is removed by rinsing with water, (3) a method in which an acid or water is added and heated, and gum substances and proteins are removed by centrifugation, (4) a method in which a lower monoalcohol is added and alcoholysis is performed to produce a carotenoid-containing fatty acid lower alkyl ester, and residual matter is then removed by rinsing with water, (5) a method in which washing is performed with a hydrophilic solvent, the carotenoid thus obtained is dissolved in cold acetone, and residual matter is removed by deposition, (6) a method in which purification is performed using a molecular distillation apparatus, and (7) a method in which an extraction is performed by means of a supercritical fluid using carbon dioxide.

Item 16. The method for stabilizing the emulsification of a liquid-form carotenoids color emulsion preparation according to item 14 or item 15, wherein the carotenoids color emulsion preparation is prepared by a method comprising (i) a process in which, if necessary an oil and fat is mixed with a carotenoids color, a carotenoids color or the above-obtained mixture is heated and dissolved so that an oil phase component is prepared, (ii) a process in which an emulsifying agent and an aqueous phase component are mixed with the oil phase component obtained in the abovementioned process (i), and (iii) a process in which the mixture obtained in the abovementioned process (ii) is emulsified.

The following aspects are included in the method of the present invention for stabilizing the emulsification of a carotenoids color emulsion preparation:

(V-1) The method for stabilizing the emulsification of a carotenoids color emulsion preparation according to any of items 14 through 16, wherein the carotenoids color used as a raw material is a color which has an acid value of 5 or less and an acetone-insoluble content of 2 wt % or less when adjusted so that the color value $E^{10\%}_{1cm}$ is 2550.

VI. Furthermore, the present invention provides the methods for suppressing neck ring formation or the deposition of insoluble matter in water-based products, as described in the following items 17 and 18:

Item 17. A method for suppressing neck ring formation or the deposition of insoluble matter in water-based products caused by the deterioration of the emulsified particles of an emulsified color preparation, wherein the water-based product is colored using the carotenoids color emulsion preparation according to any of items 2 through 7 as a colorant.

Item 18. The method for suppressing neck ring formation or the deposition of insoluble matter according to item 17, wherein the water-based product is a beverage.

VII. Furthermore, the present invention provides the use of a carotenoids color for the manufacture of a carotenoids color emulsion preparation, as described in the following items 19 and 21:

Item 19. The use of a carotenoids color of natural origin, which has an acid value of 10 or less and an acetone-insoluble content of 5 wt % or less when adjusted so that the color value $E^{10\%}_{1cm}$ is 2550, for the manufacture of a carotenoids color emulsion preparation.

Item 20. The use of a carotenoids color for the manufacture of a carotenoids color emulsion preparation according to item 19, wherein the carotenoids color is acquired by treating a carotenoid extract obtained from a carotenoid-containing animal or plant or carotenoid-producing microorganism by at least one method selected from the following methods:

(1) a method in which an extraction is performed using an oil and fat or an organic solvent, (2) a method in which hydrolysis is performed using an alkali, and residual matter is removed by rinsing with water, (3) a method in which an acid or water is added and heated, and gum substances and proteins are removed by centrifugation, (4) a method in which a lower monoalcohol is added and alcoholysis is performed to produce a carotenoid-containing fatty acid lower alkyl ester, and residual matter is then removed by rinsing with water, (5) a method in which washing is performed with a hydrophilic solvent, the carotenoid thus obtained is dissolved in cold acetone, and residual matter is removed by deposition, (6) a method in which purification is performed using a molecular distillation apparatus, and (7) a method in which an extraction is performed by means of a supercritical fluid using carbon dioxide.

Item 21. The use of a carotenoids color to manufacture a carotenoids color emulsion preparation according to item 19 or item 20, wherein the manufacture of the carotenoids color emulsion preparation comprises the following processes (i) through (iii):

(i) a process in which, if necessary an oil and fat is mixed with a carotenoids color, a carotenoids color or the above-obtained mixture is heated and dissolved so that an oil phase component is prepared, (ii) a process in which an emulsifying agent and an aqueous phase component are mixed with the oil phase component obtained in the process (i), and (iii) a process in which the mixture obtained in the process (ii) is emulsified.

The following aspect is included in the use of a carotenoids color for the manufacture of a carotenoids color emulsion preparation according to the present invention:

(VII-1) The use of a carotenoids color for the manufacture of a carotenoids color emulsion preparation according to any of items 19 through 21, wherein the carotenoids color is a color which has an acid value of 5 or less and an acetone-insoluble content of 2 wt % or less when adjusted so that the color value $E^{10\%}_{1cm}$ is 2550.

BEST MODE FOR CARRYING OUT THE INVENTION

I. Carotenoids Color Emulsion Preparation, and Carotenoids Color Used in the Manufacture of the Same The carotenoids color emulsion preparation of the present invention is a carotenoids color emulsion preparation which is emulsified using a color originating in a natural raw material that has an acid value of 10 or less and an acetone-insoluble content of 5 wt % or less when the color value $E^{10\%}_{1cm}$ is 2550, as a carotenoids color used in the manufacture of the carotenoids color emulsion preparation.

There are no particular restrictions on the carotenoids color used in the present invention, as long as this color is of natural origin. For example, a color prepared using plants or animals that contain carotenoids, microorganisms that produce carotenoids or the like as raw materials can be used. For instance, examples of plants or parts of plants that contain large quantities of carotenoids include the fruits or peels of oranges or other citrus fruits with a high carotenoid content; the rootstalk parts of root vegetables such as carrots, sweet potatoes and the like; the fruit parts of tomatoes, paprika and the like; the petals of marigold and the like; and the fruits of coconuts. Furthermore, examples of animals or parts of animals that contain large quantities of carotenoids include the shell parts of crustaceans such as shrimp, krill, crabs and the like. Moreover, examples of microorganisms that have the ability to produce carotenoids include algae such as dunaliella, hematococcus and the like, or yeasts such as phaffia, rhodotorula and the like.

In concrete terms, examples of carotenoids colors originating in these natural raw materials include orange color, carrot color, tomato color, paprika color, marigold color, palm oil carotene, krill color, dunaliella carotene, hematococcus algae color, phaffia color and the like. In particular, marigold colors are especially preferable. Furthermore, the carotenoids color emulsion preparation of the present invention may contain a single such carotenoids color, or may contain two or more such colors in arbitrary combinations.

In the present invention, the term "color value ($E^{10\%}_{1cm}$)" refers to the absorbance of a solution containing the carotenoids color at a concentration of 10 w/v % (measurement wavelength: maximum absorption wavelength of the carotenoids color, width of measurement cell: 1 cm). Ordinarily, this color value ($E^{10\%}_{1cm}$) can be determined by measuring the absorbance of a solution containing the carotenoids color at the maximum absorption wavelength in the visible region (width of measurement cell: 1 cm) of the carotenoids color, and converting this absorbance into the absorbance of a solution containing the carotenoids color at a concentration of 10 w/v %. Furthermore, in cases where a marigold color is used as the carotenoids color, the measurement of the abovementioned color value can be performed using an n-hexane solution containing the marigold color as the abovementioned solution containing the carotenoids color, and using a wavelength in the vicinity of 442 nm as the measurement wavelength.

Furthermore, in the present invention, the term "acid value" refers to the number of milligrams of potassium hydroxide required in order to neutralize the free fatty acids contained in 1 g of the carotenoids color. In concrete terms, the acid value of the carotenoids color can be calculated by the following method.

<Method Used to Calculated Acid Value>

(1) An equal amount of hot water is added to a color sample, and the obtained mixture is thoroughly mixed at 70° C.

(2) This mixture is centrifuged for 10 minutes at 1000×g, from the supernatant, sample of approximately 5 g is taken and weighed out (sample amount).

(3) 100 g of 95 vol % ethanol is added to the sample, and this mixture is agitated for 15 minutes at 50 to 60° C.

(4) The mixture is cooled to room temperature, and is titrated with an ethanol solution containing 0.1 N KOH.

(5) The pH of the mixture is measured during the titration, the inflexion point is determined, and acid value is calculated from the titer at the point using the following equation.

$$\text{Acid value} = \frac{\text{titer (ml)} \times 56.11 \times 0.1 \times 0.96}{\text{sample amount (g)}} \quad <\text{Equation 1}>$$

In regard to the carotenoids color used in the present invention, a color which is such that the acid value is 10 or less when the color is adjusted so that the color value ($E^{10\%}_{1cm}$) is 2550 is used as the color raw material of the carotenoids color emulsion preparation. Furthermore, an acid value that is a low as possible is desirable; for example, the acid value is preferably 5 or less, more preferably 1 or less, and even more preferably 0.5 or less. Since it is desirable that the acid value be as low as possible, as was described above, there is no particular restriction on the lower limit of the acid value; however, a value of approximately 0.1 may be cited as an example.

Furthermore, in the present invention, the term "acetone-insoluble" is a term that reflects the quantity of non-saponified substances such as phospholipids, gum substances, proteins, waxes, sterol and the like contained in the carotenoids color originating in the natural raw materials. The content of such acetone-insoluble (acetone-insoluble content) contained in the carotenoids color can be calculated using the following method.

<Method for Measuring Acetone-Insoluble Content>

(1) From a color sample, sample of approximately 3 g is taken and weighed out (sample amount); then, 50 ml of acetone is added to this sample and dissolved, and the sample is cooled to 5° C.

(2) This sample is centrifuged for 10 minutes at 1000×g, and the supernatant is removed. To the precipitate, 50 ml of acetone is again added, and this mixture is centrifuged. The supernatant is then removed, and the precipitate is recovered (acetone treatment, 5° C.).

(3) The abovementioned acetone treatment (5° C.) is repeated until there is almost no color in the precipitate.

(4) The acetone is removed by means of an evaporator from the precipitate recovered by the acetone treatment, and the weight of the obtained precipitate is measured (weight of acetone-treated precipitate).

(5) The content (wt %) of acetone-insoluble contained in 100 wt % of the color sample is determined using the following equation.

$$\text{Acetone-insoluble Content (wt \%)} = \frac{\text{weight of acetone-treated precipitate}}{\text{sample amount (g)}} \times 100 \quad <\text{Equation 2}>$$

In regard to the carotenoids color used in the present invention, a color which is such that the acetone-insoluble content in the color is 5 wt % or less when the color is adjusted so that the color value ($E^{10\%}_{1cm}$) is 2550 is used as the color raw material of the carotenoids color emulsion preparation. Furthermore, it is desirable that the acetone-insoluble content be as low as possible; for example, this content is preferably 2.5 wt % or less, and more preferably 2 wt % or less, and even more preferably 1 wt % or less. Since it is desirable that the acetone-insoluble content be as low as possible, as was described above, there are no particular restrictions on the lower limit of this content; however, a value of approximately 0.1 wt % may be cited as an example.

Furthermore, the abovementioned color value ($E^{10\%}_{1cm}$=2550) is used as a reference for indicating the acid value and the acetone-insoluble content of the carotenoids color used as a raw material in the manufacture of the carotenoids color emulsion preparation. Specifically, it is sufficient if the carotenoids color used as a raw material in the manufacture of the carotenoids color emulsion preparation of the present invention is a color in which the acid value and the acetone-insoluble content are in the abovementioned ranges when the color is adjusted so that the color has the abovementioned color value; it is not necessary that the carotenoids color itself used as the manufacturing raw material have the abovementioned color value. Ordinarily, it is desirable that carotenoids color which is adjusted so that the color value ($E^{10\%}_{1cm}$) is in the range of 1000 to 7500 be used in the manufacture of the carotenoids color emulsion preparation. In particular, it is desirable to use a marigold color that is adjusted so that the color value ($E^{10\%}_{1cm}$) is in the range of 2550 to 5000 in the manufacture of a marigold color emulsion preparation.

It is sufficient if the carotenoids color used in the present invention is a color which originates in a natural raw material, and which has a specified acid value and an acetone-insoluble content, e.g., an acid value of 10 or less and an acetone-insoluble content of 5 wt % or less, preferably an acid value of 5 or less and an acetone-insoluble content of 2 wt % or less, and more preferably an acid value of 2 or less and an acetone-insoluble content of 1 wt % or less, when the color is adjusted so that the color value ($E^{10\%}_{1cm}$) is 2550. Within these limits, there are no particular restrictions on the method of preparation.

For instance, conventional methods used for preparing carotenoids colors include methods comprising subjecting animals or plants containing-carotenoids or microorganisms producing-carotenoids (raw materials) such as those described above, which are "as is" (in raw form) or in dried form, if necessary are further pulverized, to the following extraction treatment:

(i) a treatment in which the carotenoids color is extracted from the raw materials using an edible oil such as soybean oil, rapeseed oil, corn oil or the like as an extraction solvent, or (ii) a treatment in which the carotenoids color is extracted from the raw materials using an organic solvent such as acetone, ethyl acetate, n-hexane or a lower aliphatic alcohol with 1 to 6 carbon atoms (e.g., ethanol or the like) as an extraction solvent, and the abovementioned organic solvent is then distilled away.

In most carotenoids colors prepared by such conventional methods, when the color value ($E^{10\%}_{1cm}$) is adjusted to 2550, the color has one of the following properties: namely, either the acid value is greater than 10, or the acetone-insoluble content is greater than 5 wt %.

The carotenoids color used in the present invention can also be prepared by appropriately combining treatment processes used in manufacture of the conventional known carotenoids colors, or by optimizing conditions (e.g., appropriately selecting the extraction solvent and extraction conditions or the like) used in the abovementioned treatment processes in accordance with the aim of achieving an acid value of 10 or less and an acetone-insoluble content of 5 wt % or less when the color value ($E^{10\%}_{1cm}$) is 2550. A method in which a carotenoid extract prepared from an animal or plant containing carotenoids or a microorganism producing carotenoids by the abovementioned known methods is further subjected to the treatments described below may be cited as an example of an appropriate preparation method.

Examples of such treatments include treatments in which the abovementioned carotenoid extract prepared from an animal or plant that contains carotenoids or a microorganism that produces carotenoids is treated by, (1) a method in which an extraction is performed using an arbitrary extraction solvent such as an oil and fat, an organic solvent or the like (extraction method), (2) a method in which hydrolysis is performed using an alkali, and residual matter is then washed away by rinsing with water (alkali hydrolysis method), (3) a method in which phosphoric acid, water or the like is added and mixed while being heated, and gum substances or proteins are then removed by centrifugation (gum removal treatment, protein removal treatment), (4) a method in which a lower alcohol is added and alcoholysis is performed to produce a carotenoid-containing fatty acid lower alkyl ester, after which residual matter is washed away by rinsing with water (alcoholysis method), (5) A method in which washing is performed with a hydrophilic solvent such as ethanol or the like, the carotenoid thus obtained is dissolved in cold acetone so that residual matter is deposited, and residual matter is then removed using a separation method such as filtration, precipitation, centrifugation or the like (deposition method), (6) a method in which purification is performed using a molecular distillation apparatus (molecular distillation method), or (7) a method in which an extraction is performed by means of a supercritical fluid using carbon dioxide (supercritical extraction method). Furthermore, these treatments may be performed singly, or two or more treatments may be used in arbitrary combinations.

Here, edible oils such as soybean oil, rapeseed oil, corn oil and the like may be cited as examples of oils or fats; and acetone, ethyl acetate, n-hexane and lower aliphatic alcohols with 1 to 6 carbon atoms (e.g., ethanol or the like) may be cited as examples of organic solvents, which can be used in the extraction method (1). In cases where an organic solvent is used as the extraction solvent, it is desirable that a treatment that distills away the extraction solvent be performed following the extraction treatment.

Examples of alkalies that can be used in the alkali hydrolysis method (2) include sodium hydroxide, potassium hydroxide, calcium hydroxide, sodium methylate and the like. Hydrolysis can be accomplished by adding an aqueous solution of such an alkali to the carotenoid extract, and mixing this mixture under heating and agitation.

To describe the gum removal treatment/protein removal treatment (3) in greater detail, this treatment can be carried out by adding one or more solvent selected from acids (such as phosphoric acid, citric acid and the like) and water to the carotenoid extract, and heating and agitating the resulting mixture.

In concrete terms, ethanol, methanol and the like may be cited as examples of lower monoalcohols that can be used in the alcoholysis method (4). Such alcoholysis can be accomplished by adding the abovementioned alcohol to the carotenoid extract, heating and agitating the resulting mixture, effecting a layer separation by allowing the mixture to stand, and then removing the alcohol layer.

The hydrophilic solvent used in the deposition method (5) may be any solvent in which the carotenoids color will not dissolve; concrete examples of such solvents include ethanol, methanol and aqueous solutions of these alcohols.

The molecular distillation method (6) and supercritical extraction method (7) can be respectively performed in accordance with commonly known methods.

Furthermore, in the abovementioned treatment methods (1) through (7), there are no particular restrictions on the treatment conditions; these methods can be performed with the treatment conditions appropriately adjusted so that a carotenoids color which has an acid value of 10 or less and an acetone-insoluble content of 5 wt % or less, preferably an acid value of 5 or less and an acetone-insoluble content of 2 wt % or less, and even more preferably an acid value of 2 or less and an acetone-insoluble content of 1 wt % or less, can be acquired when carotenoids color being prepared is adjusted so that the color value ($E^{10\%}_{1cm}$) is 2550.

Appropriate concrete preparation methods for the carotenoids color used in the present invention vary according to the type of carotenoids color and the type of natural raw material used, so that there are no particular restrictions on these methods. However, the following method may be cited using a marigold color as an example.

The dried petals of marigold are pulverized if necessary, and this preparation is soaked (warm immersion or cold immersion) in an organic solvent such as acetone, ethyl acetate, n-hexane or a lower alcohol with 1 to 6 carbon atoms (e.g., ethanol), preferably n-hexane, so that a fraction containing a carotenoids color is extracted. The organic solvent is distilled away from the extract thus obtained, and the residue is washed using a hydrophilic organic solvent such as a lower alcohol with 1 to 6 carbon atoms (preferably ethanol) or the like. Furthermore, it is desirable that this washing be performed at 20 to 75° C. Following this washing, the soluble component and insoluble component are separated using an arbitrary separation method such as centrifugation, precipitation, filtration or the like. The insoluble component thus obtained is dissolved in acetone, and is then cooled (to approximately 5° C.); the deposited residual matter is then removed by an arbitrary separation method, and the acetone-insoluble fraction is recovered. The acetone is distilled away from this acetone-insoluble fraction, and the residue is recovered as a marigold color.

Furthermore, the color value, acid value, and acetone-insoluble content of the marigold color thus obtained can be evaluated using the respective methods described above.

The carotenoids color emulsion preparation of the present invention can be prepared using the carotenoids color prepared from a natural raw material as described above as the raw material of this preparation, by emulsifying the carotenoids color. There are no particular restrictions on the emulsification method used; this emulsification can be performed using ordinary methods.

In concrete terms, the carotenoids color emulsion preparation of the present invention can be prepared using the abovementioned carotenoids color as a raw material by a method comprising (i) a process in which, an oil and fat is mixed with this color if necessary, a color or the above-obtained the mixture is heated and dissolved so that an oil phase component is prepared (oil phase component preparation process), (ii) a process in which an emulsifying agent and an aqueous phase component are mixed with this oil phase component (mixing process), and (iii) a process in which the mixture thus obtained is emulsified (emulsification process).

(i) Oil Phase Component Preparation Process

The preparation of the oil phase component can be accomplished by heating and dissolving the carotenoids color. Here, there are no particular restrictions on the heating temperature, as long as this is a temperature are which the carotenoids color dissolves or is converted from a solid into a liquid; this temperature can be appropriately set and adjusted in accordance with the kind of a carotenoids color that is used. For example, in cases where a marigold color is used as the carotenoids color, the heating temperature is 60 to 120° C., preferably 80 to 110° C., and more preferably 90 to 100° C.

Here, an oil and fat can be mixed with the oil phase component as necessary. In this case, the oil phase component can be prepared by mixing an oil and fat with the abovementioned carotenoids color, and heating and dissolving this mixture.

Oils and fats that can be used in the present invention include oils and fats that can be appropriately used in the field of food products. Examples of such oils and fats include vegetable oils such as soybean oil, rapeseed oil, corn oil, coconut oil and the like; and animal fats (including oils and fats originating in marine foods) such as beef tallow, lard, whale blubber, fish oil and the like. Furthermore, in cases where an oil and fat is used, an oil-soluble oxidation inhibitor such as extract tocopherol, synthetic dl-α-tocopherol, spice extract or the like may also be added.

In cases where an oil and fat is used, there are no particular restrictions on the amount added; for example, however, the amount added is ordinarily 0.1 to 1000 parts by weight, preferably 1 to 500 parts by weight, and more preferably 5 to 200 parts by weight, per 100 parts by weight of the carotenoids color that is the object of mixing.

Furthermore, in addition to the abovementioned oil and fat, a specific gravity adjuster may be added as an optional component to the oil phase component. There are no restrictions on such specific gravity adjusters; examples of such adjusters include sucrose fatty acid esters which have organic fatty acids with 8 to 22 carbon atoms (e.g., stearic acid, palmitic acid, myristic acid, lauric acid, capric acid, caprylic acid, oleic acid, linolic acid or the like) as a fatty acid moiety, or acetylated forms of such sucrose fatty acid esters (acetylated sucrose fatty acid esters), and SAIB (sucrose acetate isobutyrate) or the like.

Next, the oil phase component thus prepared is (ii) mixed with an emulsifying agent and an aqueous phase component (mixing process), and (iii) subjected to an emulsification treatment (emulsification process).

(ii) Mixing Process

There are no particular restrictions on the emulsifying agent that is used in the mixing process; conventional known monomolecular emulsifying agents and macromolecular emulsifying agents can be widely used. Examples of monomolecular emulsifying agents that can be used include various types of anionic and cationic surfactants, nonionic surfactants such as glycerol fatty acid esters, diglycerol fatty acid esters, sucrose fatty acid esters and the like, and amphoteric surfactants such as lecithin and the like. Examples of macromolecular emulsifying agents include natural vegetable gums such as gum arabic, gum ghatti, arabinogalactan and the like; water-soluble hemicellulose such as soybean fiber, corn fiber and the like; processed starch; dextrin; pectin; saponin; lecithin; enzyme-treated lecithin; enzymatically decomposed lecithin and the like. These emulsifying agents may be used singly, or may be use in arbitrary combinations of two or more agents.

There are no particular restrictions on the amount of this emulsifying agent that is added; ordinarily, a range in which the emulsifying agent is contained at the rate of 0.1 to 80 wt %, preferably 1 to 50 wt %, and more preferably 2 to 40 wt %, in 100 wt % of the final emulsified color preparation (calculated as a liquid-form emulsion) may be cited as an example.

Water may be cited as an example of the aqueous phase component used; however, besides water, the preparation may also contain polyhydric alcohols. Since such polyhydric alcohols are mixed with water and used in the form of a water-containing polyhydric alcohol solution, it is desirable that these polyhydric alcohols be water-soluble so that the compatibility with water is good. Concrete examples of polyhydric alcohols that can be used include dihydric alcohols such as propylene glycol and the like; trihydric alcohols such as glycerol and the like; and sugars such as maltitol, lactitol, palatinite, erythritol, sorbitol, mannitol and the like. These alcohols may be mixed with water at an arbitrary rate and used. For example, in cases where a polyhydric alcohol is added, the amount added may be appropriately selected and adjusted from a range of 50 to 300 parts by weight, preferably 100 to 300 parts by weight, per 100 parts by weight of water. If necessary, furthermore, oxidation inhibitors may also be mixed with the aqueous phase component. Here, oxidation inhibitors used as food additives may be widely used as the abovementioned oxidation inhibitors. Although there are no restrictions on the oxidation inhibitors used, examples of compounds that can be used include ascorbic acids such as L-ascorbic acid and salts of the same; erythorbic acids such as erythorbic acid and salts of the same; sulfite salts such as sodium sulfite, potassium pyrosulfite and the like; ascorbic acid esters such as ascorbyl palmitate (esters comprising ascorbic acid and palmitic acid) and the like; and various types of vegetable extracts such as Hollyhock flower extract Gossypetin, licorice oil extract, edible canna extract, clove extract, enzymatically decomposed apple extract, fennel extract with refined oil removed, horseradish extract, sage extract, parsley extract, tea extract, *Houttuynia cordata* extract, raw-coffee bean extract, sunflower seed extract, pimenta extract, grape seed extract, blueberry leaf extract, *Cyathea spinulosa/Gingko* extract, pepper extract, garden balsam extract, Chinese bayberry extract, eucalyptus leaf extract, gentian root extract, rutin extract (red bean full leaf, sophora or *Fagopyrum esculentum* full leaf extract) and the like; ellagic acid; chlorogenic acid; enzyme-treated rutin; rutin decomposition products (quercetin); rutin enzymatic decomposition products (isoquercitrin), enzyme-treated isoquercitrin; rapeseed oil extract; rice bran oil extract; rice bran enzymatic decomposition products and the like.

There are no particular restrictions on the amount of the aqueous phase component that is mixed; ordinarily, however, a content in the range of 50 to 99 wt %, preferably 60 to 95 wt %, and more preferably 70 to 90 wt % relative to 100 wt % of the final emulsified color preparation, may be cited as an example.

The mixing process can be accomplished by mixing the oil phase component prepared in the abovementioned process (i) with the abovementioned emulsifying agent and aqueous phase component. There are no particular restrictions on the mixing method; this mixing can be accomplished by agitation using an ordinary agitator. There are likewise no particular restrictions on the temperature conditions during mixing. Ordinarily, this temperature can be appropriately selected from temperatures in the range of room temperature to 60° C., preferably 20 to 60° C.

Furthermore, there are no particular restrictions on the amount of the oil phase component that is mixed; ordinarily, however, the amount of the oil phase component in 100 wt % of the final emulsified color preparation (calculated as a liquid-form emulsion) is 0.5 to 50 wt %, preferably 1 to 40 wt %, and more preferably 2 to 35 wt %.

(iii) Emulsification Process

The mixture containing at least an oil phase component, emulsifying agent and aqueous phase component obtained in the abovementioned mixing process (ii) is next subjected to an emulsification process. Here, there are no particular restrictions on the emulsification treatment; this treatment can be performed using customary methods. For example, emulsification can be accomplished by agitating and mixing the oil phase component, emulsifying agent and aqueous phase component, and this emulsifying this mixture using a conventionally known emulsifying apparatus such as colloid mill, high-pressure homogenizer, microfluidizer, nanomizer, homo-mixer, dispermill, ultrasonic emulsifying apparatus, film emulsifying apparatus or the like.

The emulsified color preparation obtained by such an emulsification treatment has a liquid-form; however, this preparation may be adjusted to a solid-form (e.g., powder form, granular form or the like) by further subjecting the preparation to a drying process or drying and granulation process. There are no particular restrictions on drying methods that can be used; for example, spray drying methods using a spray drier or the like, vacuum drying methods, freeze-drying methods or the like may be used as desired. There are likewise no particular restrictions on granulation methods that can be used; wet granulation methods comprising a treatment such as fluid motion, rolling motion, pulverization, spray or agitation methods or the like, or dry granulation methods, may be used as desired.

Accordingly, the carotenoids color emulsion preparation of the present invention may be a liquid-form preparation, a preparation adjusted to a powder form by further subjecting this liquid-form preparation to a drying treatment, or a preparation adjusted to a granular form by means of a drying and granulation treatment. Specifically, in the present invention, the term "carotenoids color emulsion preparation" refers comprehensively to a color preparation prepared by a method comprising an emulsification treatment; there are no particular restrictions on the final configuration of this preparation.

Furthermore, the emulsified color preparation of the present invention, especially the abovementioned granular emulsified color preparation, may be prepared by mixing diluents, carriers or other additives as other components in the abovementioned granulation treatment. Such diluents, carriers and additives may include a wide variety of substances generally used in color preparations, especially emulsified color preparations, as long as these substances do not hinder the effect of the present invention. Examples of such substances include sucrose, glucose, dextrin, gum arabic, water, ethanol, propylene glycol, glycerol, glucose syrup and the like.

Even in cases where the carotenoids color emulsion preparation of the present invention prepared as described above has a liquid-form configuration, the preparation itself is extremely superior in terms of emulsion stability, as is shown in Experimental example 1 described later, so that problems such as separation due to variation in the emulsified particles or deterioration of the emulsified particles tend not to occur even in the case of long-term storage. As a result, furthermore, the preparation can stably contain a large quantity of a carotenoids color at a high concentration. The carotenoids color content that can be contained in the emulsified color preparation (liquid-form emulsion) of the present invention is 0.01 to 50 wt %, preferably 0.05 to 40 wt %, and more preferably 0.1 to 30 wt %.

In the case of emulsified preparations of ordinary oily colors, if the amount of the oily color that is mixed in the preparation exceeds 5 wt %, and especially if this amount exceeds 10 wt %, the problem of separation due to variation in the emulsified particles or deterioration of the emulsified particles as a result of long-term storage tends to occur. The emulsified color preparation of the present invention is extremely useful in that such problems tend not to occur even if the carotenoids color is mixed with the composition at the rate of 20 wt % or greater, preferably 15 wt % or greater, and more preferably 10 wt % or greater, with 50 wt % as an appropriate upper limit.

II. Colored Product

The carotenoids color emulsion preparation of the present invention can be widely used to color various types of products such as food products, drugs, quasi-drugs, cosmetics, products for daily use, feedstuffs or the like, regardless of whether these products are water-based or oil-based products.

Specifically, the present invention provides various types of products such as food products, drugs, quasi-drugs, cosmetics, products for daily use, feedstuffs the like which are colored using the abovementioned carotenoids color emulsion preparation of the present invention as a colorant.

Here, examples of cosmetics include skin cosmetics (lotions, emulsions, creams and the like), lipsticks, anti-sunburn cosmetics, makeup cosmetics and the like; examples of drugs include various types of tablets, capsules, drinkable agents, troches, gargles and the like; examples of quasi-drugs include toothpastes, mouthwashes, bad breath preventive agents and the like; examples of products for daily use include solid soaps, liquid soaps, shampoos, conditioners and the like; and examples of feedstuffs include pet foods such as cat foods, dog foods and the like, feeds for aquarium fish or cultured fish, and the like. However, the present invention is not limited to such products.

The product of the present invention is preferably a food product. There are no particular restrictions on such food products, as long as these food products are products that can be colored with a carotenoids color. Examples of such food products include frozen desserts (entremets froids) such as ice cream, ice milk, lacto-ice, sherbets (sorbets), ice candies, ice cakes (glace) and the like; beverages such as milk beverages, lactic acid bacteria beverages, soft drinks, carbonated beverages, fruit juice drinks, vegetable juice drinks, vegetable/fruit beverages, powdered beverages, jelly beverages, alcoholic beverages, coffee beverages, red tea beverages, green tea beverages, blended beverages, sports beverages, supplement beverages and the like; desserts, such as puddings (e.g., custard puddings, souffle puddings, milk puddings, puddings containing fruit juice and the like), jellies, babaloa, yogurt and the like; gum such as chewing gum, bubble gum and the like (stick gum and sugar-coated gum balls); chocolates such as coated chocolates (e.g., marble chocolates and the like), flavored chocolates (e.g., strawberry chocolates, blueberry chocolates, melon chocolates and the like) and the like; candies such as hard candies (including bonbons, butterballs, marbles, taffy, drops and the like), soft candies (including caramels, nougats, gummy candies, marshmallows and the like) and the like; baked confections such as hard biscuits, cookies, crackers, okaki (rice crackers), sembei (rice crackers), bar-form confections (e.g., cereal bars, nougat bars and the like), puff snacks and the like; soups such as consommé soups, potage soups and the like; pickles such as lightly-pickled vegetables; vegetables pickled in soy sauce, salt, miso, sake cake, rice malt, rice bran paste, vinegar, mustard, moromi and the like; pickled plums (ume-zuke), fukujin-zuke, siba-zuke, pickled gingers (shouga-zuke), vegetables pickled in plum vinegar (umesu-zuke) and the like; sauces such as separate dressings, non-oil dressings, ketchup, thick sauces, ordinary sauces and the like; jams such as strawberry jam, blueberry jam, marmalade, apple jam, apricot jam, preserves and the like; fruit wines such as red wines and the like; processed fruits such as cherries, apricots, applies, strawberries or peaches preserved in syrup, and the like; processed meats such as ham, sausage, roast pork and the like; processed marine products such as fish ham, fish sausage, fish fillets, kamaboko (steamed fish paste), chikuwa (baked fish paste), hanppen (fish minced and steamed), satsumaage (fried fish ball), datemaki (omelet wrappers), whale bacon and the like; dairy and oil & fat products such as butter, margarine, cheese, whipped cream and the like; noodles such as udon (wheat noodle), hiyamugi, somen (fine noodle), soba (buckwheat noodle), Chinese noodle, spaghetti, macaroni, bifun (rice noodle), harusame (bean-jelly stick), wonton and the like; and various other processed food products such as various types of side dishes, wheat gluten cake, denbu and the like. The product of the present invention is preferably a water-based food product such as a beverage, frozen desserts or the like, and is most preferably a beverage.

The amount of the carotenoids color emulsion preparation of the present invention that is used on various types of objects to be colored, such as food products, cosmetics, drugs, quasi-drugs, products for daily use, feedstuffs or the like, varies according to the type and purpose of the product and the desired color tone, so that this amount cannot be fixed in definite terms; however, the amount used can ordinarily be selected from the range of 0.01 to 10 wt % per 100 wt % of the product.

In the present invention, especially in cases where a color preparation containing a high concentration of a carotenoids color is used for coloring, a small amount of the color preparation is sufficient; accordingly, the following advantage is obtained: namely, the colored product that is prepared does not have any odorization caused by the color preparation. Furthermore, if the carotenoids color emulsion preparation of the present invention is used as the colorant of the present invention, the occurrence of problems such as the deposition or precipitation of insoluble matter, or the formation of a neck ring during long-term storage or under harsh conditions such as the conditions of a sterilization treatment or the like can be significantly suppressed, especially in cases where the carotenoids color emulsion preparation of the present invention is used in water-based products, e.g., food products such as beverages, frozen desserts or the like; cosmetics such as lotions, emulsions or the like; or drugs or quasi-drugs such as drinkable agents, liquid-form mouthwashes, liquid toothpastes or the like.

III. Method for Manufacturing Carotenoids Color Emulsion Preparation

The present invention provides a method for manufacturing the abovementioned carotenoids color emulsion preparation. In concrete terms, the method can be accomplished by using a carotenoids color of natural origin which has an acid value of 10 or less and an acetone-insoluble content of 5 wt % or less when adjusted so that the color value $E^{10\%}_{1cm}$ is 2550 as a raw material, and performing (i) a process in which, an oil and fat is added as necessary to the carotenoids color, this carotenoids color or the above-obtained mixture is heated and dissolved to prepare an oil phase component (oil phase component preparation process), (ii) a process in which an emulsifying agent and an aqueous phase component are mixed with this oil phase component (mixing process), and (iii) a process in which the mixture thus obtained is emulsified (emulsification process).

In regard to the carotenoids color used as a raw material, the method used to prepare this carotenoids color, and the abovementioned processes, i.e., (i) oil phase component preparation process, (ii) mixing process and (iii) emulsification process, the detailed description given above in section I (Carotenoids color Emulsion Preparation, and Carotenoids color Used in the Manufacture of the Same) can also be applied here.

IV. Method for Stabilizing the Emulsification of the Carotenoids Color Emulsion Preparation The present invention provides a method for stabilizing the emulsification of the abovementioned carotenoids color emulsion preparation.

The stabilization of the emulsification of the abovementioned carotenoids color emulsion preparation can be accomplished by preparing the emulsified color preparation using a carotenoids color of natural origin which has an acid value of 10 or less and an acetone-insoluble content of 5 wt % or less when adjusted so that the color value $E^{10\%}_{1cm}$ is 2550 as the raw-material color. In concrete terms, this method can be accomplished by using the abovementioned carotenoids color as a color raw material, and performing (i) a process in which, an oil and fat is added as necessary to the carotenoids color, the carotenoids color or the obtained-mixture is heated and dissolved to prepare an oil phase component (oil phase component preparation process), (ii) a process in which an emulsifying agent and an aqueous phase component are mixed with this oil phase component (mixing process), and (iii) a process in which the mixture thus obtained is emulsified (emulsification process).

Here as well, in regard to the carotenoids color used as a raw material, the method used to prepare this carotenoids color, and the abovementioned processes ((i) oil phase component preparation process, (ii) mixing process and (iii) emulsification process), the detailed description given above in section I (Carotenoids color Emulsion Preparation and Carotenoids color used in the Manufacture of the Same) can be applied "as is".

V. Method for Suppressing Neck Ring Formation or Deposition of Insoluble Matter in colored Water-Based Products The present invention provides a method for suppressing neck ring formation or the deposition of insoluble matter caused by deterioration of the emulsified particles of the emulsified preparation occurring in cases where water-based products are colored using the carotenoids color emulsion preparation.

This method can be performed by using the abovementioned carotenoids color emulsion preparation of the present invention as a carotenoids color emulsion preparation.

In concrete terms, this method can be performed by coloring a water-based product using a carotenoids color emulsion preparation that is prepared by emulsifying a carotenoids color of natural origin which has an acid value of 10 or less and an acetone-insoluble content of 5 wt % or less when adjusted so that the color value $E^{10\%}_{1cm}$ is 2550. Furthermore, the coloring can be accomplished by using the abovementioned carotenoids color emulsion preparation of the present invention as one of the raw materials of the water-based product. The concrete operation can be performed using conventional methods in accordance with the type of product that is being colored.

Here, there are no particular restrictions on the colored water-based product that is the object of the present invention. Water-based products belonging to the categories of food products, drugs, quasi-drugs, cosmetics, products for daily use, feedstuffs or the like may be arbitrarily cited as examples. In concrete terms, water-based products, e.g., food products such as beverages, frozen desserts and the like; cosmetics such as lotions, emulsions and the like; and drugs or quasi-drugs such as drinkable agents, liquid-form mouthwashes, liquid toothpastes and the like may be cited as examples. Here, furthermore, in regard to the types and the proportions used of the carotenoids color emulsion preparation that is used as a colorant, the detailed description given above in section I (Carotenoids color Emulsion Preparation and Carotenoids color used in the Manufacture of the Same) can be applied "as is".

EXAMPLES

Below, examples and comparative examples will be described in order to make the constitution and effects of the present invention even clearer. However, the present invention is not affect by these examples or the like. Furthermore, in regard to the units of the compositions described below, all parts are parts by weight unless otherwise specifically noted.

Example 1

Preparation of Marigold Color

Flower petals of the marigold plant were dried and extracted with n-hexane, and from the extract thus obtained, the n-hexane was then distilled away, so that a marigold extract was acquired. To 100 parts of this extract (color value=2500) 100 parts of 95 vol % ethanol was added, and this mixture was mixed for 30 minutes at 60° C. This mixture was then allowed to stand for 1 hour at the same temperature. Afterward, the supernatant was removed, and the precipitate was recovered. To this precipitate, 200 parts of acetone was added and mixed so that the precipitate was dissolved. This solution was then cooled to 5° C., and added a filter material to filter out the insoluble matter by a filter paper (filter cloth).

Next, the acetone was distilled away from the filtrate thus obtained, thus producing 30 parts of a marigold color. The color value of this color was 6500; when this color value was adjusted to 2550, the acid value was 0.5, and the acetone-insoluble content was 0.4.

Example 2

Marigold Color Emulsion Preparation (No. 1)

Five parts of the marigold color of natural origin prepared by the method described in Example 1, 0.2 parts of extract tocopherol, 5 parts of coconut oil and 9.7 parts of SAIB (sucrose acetate isobutyrate) were mixed, and this mixture was heated and dissolved at 100° C., thus producing an oil phase component. Meanwhile, 20 parts of gum arabic, 0.1 parts of L-ascorbic acid and 10 parts of propylene glycol were mixed with 50 parts of water and dissolved, thus producing an aqueous phase component. The abovementioned oil phase component was mixed with this aqueous phase component, and this mixture was emulsified at a pressure of 450 kg/cm² using a high-pressure homogenizer, thus producing a liquid-form marigold color emulsion preparation (liquid-form emulsion).

Example 3

Marigold Color Emulsion Preparation (No. 2)

Fifteen parts of the marigold color prepared by the method described in Example 1, 0.5 parts of extract tocopherol and 14.5 parts of salad oil were mixed, and this mixture was heated and dissolved at 100° C., thus producing an oil phase component. Meanwhile, 20 parts of gum arabic, 45 parts of dextrin and 5 parts of L-ascorbic acid were mixed with 150 parts of water and dissolved, thus producing an aqueous phase component. The abovementioned oil phase component was mixed with this aqueous phase component, and this mixture was emulsified using a dispermill (flow rate 200 kg/hr). The resulting emulsion was then spray-dried using a spray drier, thus producing a powdered marigold color emulsion preparation (powder).

Comparative Example 1

A liquid-form marigold color emulsion preparation (liquid-form emulsion) was prepared in the same manner as in Example 1, except for the fact that a marigold color which had an acid value of 20 and an acetone-insoluble content of 9.8 wt % when adjusted so that the color value $E^{10\%}_{1cm}$ was 2550 was used (Comparative Product 1)

Comparative Example 2

A liquid-form marigold color emulsion preparation (liquid-form emulsion) was prepared in the same manner as in Example 1, except for the fact that a marigold color which had an acid value of 16.5 and an acetone-insoluble content of 3.5 wt % when adjusted so that the color value $E^{10\%}_{1cm}$ was 2550 was used (Comparative Product 2).

Comparative Example 3

A liquid-form marigold color emulsion preparation (liquid-form emulsion) was prepared in the same manner as in Example 1, except for the fact that a marigold color which had an acid value of 3.7 and an acetone-insoluble content of 14.5 wt % when adjusted so that the color value $E^{10\%}_{1cm}$ was 2550 was used (Comparative Product 3).

Experimental Example 1

Storage Stability (Emulsion Stability) of Color Emulsion Preparation

The color preparation (Product 1 of the Present Invention) prepared in the abovementioned Example 2 and the Comparative Products 1, 2 and 3 prepared in Comparative Examples 1, 2 and 3 were stored for 2 hours at 60° C. immediately following emulsification, and the state of the emulsified particles and particle size distribution before and after storage were evaluated by microscopic observation. The results are shown in Table 1. The measurement of the particle size distribution was performed using the Laser Diffraction Particle Size Analyzer SALD-1100 manufactured by SHIMADZU CORPORATION.

formation or deposition (precipitation) of insoluble matter even after being allowed to stand for 1 month, and was thus superior in terms of storage stability.

TABLE 1

|  | Storage at 60° C. | Particle size distribution | | | Microscopic observation State of emulsified particles |
|---|---|---|---|---|---|
|  |  | Median distribution | Particle size range | Proportion of particles with a size of 1.3 μm or greater |  |
| Product 1 of the Present Invention | Before | 0.52 | 0.3-1.3 | 0% | Uniform |
|  | After | 0.52 | 0.3-1.3 | 0% | Uniform |
| Comparative Product 1 | Before | 0.70 | 0.3-3.7 | 20.8% | Variation seen |
|  | After | 1.07 | 0.3-3.7 | 39.6% | Particle deterioration, considerable variation |
| Comparative Product 2 | Before | 0.60 | 0.3-2.6 | 12.9% | Variation seen |
|  | After | 0.80 | 0.3-3.7 | 25.4% | Variation considerable |
| Comparative Product 3 | Before | 0.77 | 0.3-3.7 | 25.6% | Variation seen |
|  | After | 0.92 | 0.3-3.7 | 33.7% | Variation considerable |

It is seen from these results that the carotenoids color emulsion preparation of the present invention (Product 1 of the Present Invention) showed uniform emulsified particles immediately following emulsification, and that no change in the particles was seen even after the preparation was stored for 2 hours at 60° C. On the other hand, the comparative examples all showed variation in the emulsified particles from the time immediately following emulsification. In particular, samples in which the acid value was greater than 10, and the acetone-insoluble content was greater than 5 wt %, showed the worst state. Furthermore, samples in which either the acid value was greater than 10 or acetone-insoluble content was greater than 5 wt % showed a low stability. After storage for 2 hours at 60° C., the variation was also increased as a result of deterioration of the emulsified particles. It was confirmed from these results that the carotenoids color emulsion preparation of the present invention is superior in terms of emulsion stability, and that this preparation shows no change in the emulsified state even in the case of long-term storage.

Experimental Example 2

One hundred thirty parts of a high fructose corn syrup and 2 parts of citric acid were dissolved in 120 parts of water, and to the solution thus obtained, 1 part of either Product 1 of the Present Invention or Comparative Product 1 as a carotenoids color emulsion preparation was added. The total amount of the solution was then adjusted to 1000 parts with pure water. Carbon dioxide gas was blown into this solution and mixed; bottles were then filled with this product and sterilized for 20 minutes at 85° C., thus producing a carbonated beverage. This beverage was allowed to stand for 1 month at 25° C., and the condition of the beverage was then observed. As a result, it was found that the comparative beverage prepared using Comparative Product 1 as the carotenoids color emulsion preparation showed neck ring formation and the deposition (precipitation) of insoluble matter when allowed to stand for 1 month, so that this product have no commercial value. On the other hand, the beverage of the present invention prepared using Product 1 of the Present Invention showed no neck ring

| Manufacture Example 1 Pineapple Jelly | |
|---|---|
| 1. Sugar | 8.0 (kg) |
| 2. Powdered glucose syrup | 10.0 |
| 3. Polysaccharide thickener | 1.0 |
| 4. Pineapple juice | 2.0 |
| 5. Citric acid | 0.2 |
| 6. L-Ascorbic acid | 0.02 |
| 7. Pineapple flavor | 0.15 |
| 8. Marigold color preparation (Example 2) | 0.04 |
| 9. Water | remainder |
| Total | 100.00 (kg) |

While the water was agitated, a powdered mixture consisting components 1, 2 and 3 was added, and this mixture was heated and dissolved for 10 minutes at 80° C. Components 4 through 8 were added to this, and the resulting mixture was agitated. A container was filled with this mixture, and sterilization was performed for 30 minutes at 85° C. This was then cooled to produce a pineapple jelly. The pineapple jelly thus obtained showed no unpleasant odor originating in the emulsified color preparation, and showed a stable color tone over a long period of time, with no color fading being observed.

| Manufacture Example 2 Pound Cake | |
|---|---|
| 1. Soft flour | 120 (kg) |
| 2. Sugar | 100 |
| 3. Salt-free butter | 100 |
| 4. Whole eggs | 100 |
| 5. White rum (rum) | 10 |
| 6. Lemon juice | 2 |
| 7. Marigold color preparation (Example 2) | 0.4 |
| 8. Lemon fragrance | 0.4 |
| Total | 432.8 (kg) |

Component 3 was formed into a cream using a whipper. Components 2 and 4 were added and mixed with this component 3; then, component 1 was added and mixed. Next, components 5 through 8 were added and uniformly mixed. This mixture was poured into cake molds, and was baked for 50 minutes at 160° C. in an oven. The pound cake thus obtained showed no particular degeneration of the color caused by heating, and showed a stable color tone.

| Manufacture Example 3 Hard Candy | |
|---|---|
| 1. Sugar | 60 (kg) |
| 2. glucose syrup | 40 |
| 3. Water | 20 |
| 4. Citric acid | 0.4 |
| 5. L-Ascorbic acid | 0.01 |
| 6. Marigold color preparation (Example 2) | 0.02 |
| 7. Pineapple fragrance | 0.15 |
| Weight following preparation: | 100.00 (kg) |

Components 1 through 3 were mixed and heated to 155° C., and these components were dissolved. This mixture was cooled to 125° C.; then, components 4 through 7 were added and mixed, and this mixture was molded to produce a hard candy. The hard candy thus obtained showed no unpleasant odor, and the color tone also showed long-term stability.

| Manufacture Example 4 Lemon Sherbet | |
|---|---|
| 1. Sugar | 19 (kg) |
| 2. Powdered glucose syrup | 3.5 |
| 3. Citric acid | 0.25 |
| 4. Lemon juice | 5 |
| 5. Marigold color preparation (Example 2) | 0.08 |
| 6. Lemon fragrance | 0.15 |
| 7. Water | remainder |
| Total | 100.00 (kg) |

Components 1 and 2 were mixed as powders; then, water was added, and sterilization was performed for 10 minutes at 85° C. This mixture was cooled to 5° C., and was aged. Components 3 through 6 were added and mixed, and freezing was performed at an overrun of 40%, thus producing a lemon sherbet. The sherbet thus obtained maintained a stable color tone over a long period of time.

| Manufacture Example 5 Banana Gummy Candy | |
|---|---|
| 1. Gelatin | 8 (kg) |
| 2. Water | 16 |
| 3. Sugar | 25 |
| 4. glucose syrup | 40 |
| 5. Sorbitol | 20 |
| 6. Water | 9 |
| 7. Citric acid | 0.7 |
| 8. L-Ascorbic acid | 0.05 |
| 9. Marigold color preparation (Example 2) | 0.12 |
| 10. Banana juice | 1 |
| 11. Banana fragrance | 0.1 |
| Total | 100.0 (kg) |

Component 1 was thoroughly swelled with water (Component 2), and was then heated and dissolved. Components 3 through 6 were boiled down to Brix 85°; gelatin was added to this mixture, and components 7 through 11 were added in that order. The mixture was cooled to approximately 80° C.; bubbles were allowed to float to the top and were removed. A starch mold was filled with this mixture, and the mixture was dried, thus producing a gummy candy. The gummy candy thus obtained was able to maintain a stable color tone over a long period of time, and showed no unpleasant odor originating in the color.

| Manufacture Example 6 Lemon Beverage | |
|---|---|
| 1. high fructose corn syrup | 13.3 (kg) |
| 2. Vitamin C | 0.1 |
| 3. Citric acid | 0.2 |
| 4. Marigold color preparation (Example 2) | 0.1 |
| 5. Lemon fragrance | 0.1 |
| 6. Water | remainder |
| Total | 100.00 (kg) |

Components 1 through 6 were mixed, and water was added to produce a liquid beverage preparation. Bottles were filled with this preparation, and sterilization was performed for 10 minutes at 85° C. This product was then cooled to 5° C. and allowed to stand. Even after being cooled and allowed to stand, the beverage showed no deposition of insoluble matter, neck ring formation or the like. Furthermore, even when the beverage was allowed to stand at room temperature, no unpleasant odor was detected, and a stable color tone was maintained over a long period of time.

INDUSTRIAL APPLICABILITY

The carotenoids color emulsion preparation of the present invention is in itself superior in terms of emulsion stability, and can therefore be provided as a preparation that stably contains a larger amount of a carotenoids color. Specifically, the present invention makes it possible to provide a color preparation which contains a carotenoids color prepared from a natural raw material at a high concentration. As a result, the amount used in coloring can be decreased, so that problems of odor or taste originating in the base agent or the like of the color preparation can be eliminated.

Furthermore, the carotenoids color emulsion preparation of the present invention is a preparation that is superior in terms of stability, which shows no problems such as deposition of insoluble matter or neck ring formation even when applied to water-based products such as beverages or the like. Accordingly, products prepared by mixing this color preparation can be provided as products with superior stability, which show no problems such as deposition of insoluble matter or neck ring formation even in the case of long-term storage or sterilization treatments.

The invention claimed is:

1. A method for suppressing neck ring formation or the deposition of insoluble matter in water-based products caused by the deterioration of the emulsified particles of an emulsified color preparation, comprising coloring the water-based product using a marigold color emulsion preparation obtained by emulsifying a natural marigold color which has an acid value of 10 or less and an acetone-insoluble content of 5 wt % or less when adjusted so that the color value $E^{10\%}_{1cm}$ is 2550.

2. The method for suppressing neck ring formation or the deposition of insoluble matter according to claim 1, wherein the water-based product is a beverage.

3. The method for suppressing neck ring formation or the deposition of insoluble matter according to claim 1, wherein the marigold color emulsion preparation is obtained by a method comprising the following processes:
- (i) a process in which the marigold color is heated and dissolved so that an oil phase component is prepared,
- (ii) a process in which an emulsifying agent and an aqueous phase component are mixed with the oil phase component obtained in the abovementioned process (i), and
- (iii) a process in which the mixture obtained in the abovementioned process (ii) is emulsified.

4. The method for suppressing neck ring formation or the deposition of insoluble matter according to claim 2, wherein the marigold color emulsion preparation is obtained by performing further (iv) a process in which the emulsified product obtained in the abovementioned process (iii) is dried, or a process in which this product is dried and granulated.

5. The method for suppressing neck ring formation or the deposition of insoluble matter according to claim 1, wherein the marigold color emulsion preparation is a liquid-form, powder-form or granular configuration.

6. The method for suppressing neck ring formation or the deposition of insoluble matter according to claim 1, wherein the marigold color emulsion preparation contains a marigold color at the rate of 0.01 to 50 wt %.

7. The method for suppressing neck ring formation or the deposition of insoluble matter according to claim 1, wherein the marigold color emulsion preparation is obtained by a method comprising the following processes:
- (i) a process in which an oil and fat are mixed with the marigold color, and the above-obtained mixture is heated and dissolved so that an oil phase component is prepared,
- (ii) a process in which an emulsifying agent and an aqueous phase component are mixed with the oil phase component obtained in the abovementioned process (i), and
- (iii) a process in which the mixture obtained in the abovementioned process (ii) is emulsified.

* * * * *